United States Patent
Li et al.

(10) Patent No.: US 11,150,232 B2
(45) Date of Patent: Oct. 19, 2021

(54) LABORATORY DEVICE AND METHOD FOR SIMULATING CEMENT SHEATH CONSOLIDATION IN FROZEN SOIL STRATA

(71) Applicant: China University of Petroleum (East China), Qingdao (CN)

(72) Inventors: Xiaorong Li, Qingdao (CN); Chuanliang Yan, Qingdao (CN); Yang Li, Qingdao (CN); Yuanfang Cheng, Qingdao (CN); Zhongying Han, Qingdao (CN); Benjian Song, Qingdao (CN); Xiaohui Zhou, Qingdao (CN)

(73) Assignee: CHINA UNIVERSITY OF PETROLEUM (EAST CHINA), Qingdao (CN)

( * ) Notice: Subject to any disclaimer, the term of this patent is extended or adjusted under 35 U.S.C. 154(b) by 355 days.

(21) Appl. No.: 16/455,789

(22) Filed: Jun. 28, 2019

(65) Prior Publication Data
US 2020/0003751 A1 Jan. 2, 2020

(30) Foreign Application Priority Data

Jun. 28, 2018 (CN) .......................... 201810683622.7

(51) Int. Cl.
| | |
|---|---|
| *G01N 33/00* | (2006.01) |
| *G01N 33/38* | (2006.01) |
| *E21B 41/00* | (2006.01) |
| *G01N 3/02* | (2006.01) |
| *E21B 33/14* | (2006.01) |

(52) U.S. Cl.
CPC .......... *G01N 33/383* (2013.01); *E21B 41/00* (2013.01); *G01N 3/02* (2013.01); *E21B 33/14* (2013.01)

(58) Field of Classification Search
CPC ........ G01N 33/383; G01N 3/02; E21B 41/00; E21B 33/14
See application file for complete search history.

(56) References Cited

U.S. PATENT DOCUMENTS

| | | | |
|---|---|---|---|
| 7,549,320 B2* | 6/2009 | Funkhouser | G01N 3/10 73/37 |
| 2006/0067162 A1* | 3/2006 | Blankinship | E21B 47/005 367/35 |
| 2015/0034311 A1* | 2/2015 | Tunget | E21B 47/12 166/250.14 |
| 2018/0045581 A1* | 2/2018 | Goda | G01K 7/04 |
| 2018/0066510 A1* | 3/2018 | Walker | E21B 47/16 |

\* cited by examiner

*Primary Examiner* — Jamel E Williams
(74) *Attorney, Agent, or Firm* — Bayramoglu Law Offices LLC

(57) ABSTRACT

A laboratory device for simulating the cement sheath consolidation in the frozen soil strata includes the main body, the pressure system and the measuring system. The main body includes the fixing plate, the detachable plate and the base plate. The circular hole is provided in the center of the base. The central column or the heat insulating casing is mounted on the base through the circular hole. The fixing plate, the detachable plate, the base plate and the central column or the heat insulating casing form a cavity for preparing the core and the cement sheath. During use, the device is placed in a low temperature context, and then the frozen soil core with a hollow cylinder can be artificially fabricated. Further, the heat insulating casing holder is placed, and the cement is added to simulate the state of the cement sheath consolidation under the actual strata conditions.

20 Claims, 5 Drawing Sheets ical field

LABORATORY DEVICE AND METHOD FOR SIMULATING CEMENT SHEATH CONSOLIDATION IN FROZEN SOIL STRATA

CROSS REFERENCE TO THE RELATED APPLICATIONS

This application is based upon and claims priority to Chinese Patent Application No. CN 201810683622.7, filed on Jun. 28, 2018, the entire contents of which are incorporated herein by reference.

TECHNICAL FIELD

The present invention relates to a laboratory device for simulating a cement sheath consolidation, in particular to a laboratory device and a method for simulating a cement sheath consolidation in frozen soil strata, which belongs to the field of oil and gas well cementing.

BACKGROUND

With the development of the petroleum industry and the increasingly expanding demand for energy, it became a point of focus to explore and exploit the unconventional oil and gas resources. In 2008, USGS (United States Geological Survey) issued a report affirmative of the rich oil and gas resources in the Arctic region. For various countries in the world, the exploration and exploitation of polar oil and gas resources is on the agenda. Enormous potentials of the oil and gas exploration are contained in the frozen soil regions of Tibetan Plateau and Junggar Basin in China. Therefore, it is extremely urgent to study the exploration and exploitation technique for oil and gas in the frozen soil strata, especially the well cementing technique in the frozen soil strata. At present, the research on the casing well cementing technique lays most emphasis on the conventional land drilling and deep water drilling, while few researches on the well cementing technique in frozen soil strata exist. The well cementing technology in frozen soil strata greatly differs from that in the conventional drilling. First of all, the strength of the cement sheath grows slowly due to the low temperature in the frozen soil strata, and the cement sheath is compressed all the time due to the creep characteristic of the frozen soil, which may cause crushing damage to the cement sheath. Secondly, the water in the cement slurry is consolidated due to the low temperature, thereby failing to consolidate with the cement under the hydration effect. Third, a large amount of heat is released due to the cement consolidation, which will thaw the partial frozen soil, further affecting the consolidation and cementation of cement with the strata. Consequently, the experimental research on the consolidation degree of cement in the consolidation process of the cement sheath in the frozen soil strata, the stress action between the strata and the cement sheath, and the effect of heat released by the cement consolidation on the temperature of the frozen soil strata are crucial for the exploration and exploitation of oil and gas in the frozen soil strata. Meanwhile, the coring of the frozen soil strata is very difficult and expensive, and the strata are subjected to gravity with a small tectonic action, which allows to replace the natural core with the artificial frozen soil sample. Therefore, in the present invention, the laboratory device for simulating the cement sheath consolidation in the frozen soil strata is applied to the lab research on the consolidation process of the cement sheath in the frozen soil strata.

SUMMARY

The objective of the present invention is to provide a laboratory device and a method for simulating a cement sheath consolidation in frozen soil strata, so as to overcome the above-mentioned deficiencies in the prior art.

In order to achieve the above-mentioned objective, the following technical solutions are proposed by the present invention.

A laboratory device for simulating a cement sheath consolidation in a frozen soil strata includes a main body, a pressure system and a measuring system.

The main body includes fixing plates, detachable plates and a base plate, wherein a circular hole is provided in a center of a base holder; a central column or a heat insulating casing is mounted on the base through the circular hole; a cavity for preparing a core and a cement sheath is formed by the fixing plate, the detachable plate, the base plate and the central column or the heat insulating casing; the detachable plate includes limiting plates and a pressure transmitting plate.

The pressure system includes an axial pressure pressurizing device and confining pressure pressurizing devices, wherein the axial pressure pressurizing device is located above the cavity, and the confining pressure pressurizing device is located outside the detachable plate.

The measuring system includes acoustic wave transmitters, acoustic wave receivers, temperature sensors and strain gauges, wherein the measuring system is connected to a controller; the acoustic wave transmitter is mounted on the fixing plate; the acoustic wave receivers and the strain gauges are mounted on the heat insulating casing; the temperature sensor is mounted on the base plate; two groups of the acoustic wave transmitters, the acoustic wave receivers, the temperature sensors, and the strain gauges are provided, respectively in directions of a maximum horizontal principal stress and a minimum horizontal principal stress, namely, pressurization directions of the two confining pressure pressurizing devices.

The main body, the pressure system and the measuring system are placed in a cooling device during operation.

Preferably, the main body is square; sides of the main body are composed of two detachable plates and two sets of fixing plates; the two detachable plates are adjacently arranged; a bottom steel plate is provided above the base plate; a heat insulating layer is provided between the base plate and the bottom steel plate; a cavity is formed by the two sets of adjacent fixing plates, two adjacent detachable plates, the bottom steel plate, and the central column or the heat insulating casing.

Preferably, the fixing plates include first fixing plates and second fixing plates, wherein one of the first fixing plates and one of the second fixing plates form a set of fixing plates; the first fixing plate and the second fixing plate are arranged in parallel; the second fixing plate is located between the first fixing plate and a housing; and a plurality of first grooves and second grooves are provided on the first fixing plate and the second fixing plate.

Preferably, the housing is provided on the sides of the main body, and the confining pressure pressurizing devices are located between the detachable plates and the housing.

Preferably, the controller is a computer.

Preferably, a first circular hole, a second circular hole and a third circular hole are respectively provided in centers of the base plate, the bottom steel plate and the heat insulating layer; the central column or the heat insulating casing is located at a center of the cavity; a longitudinal section of the central column is inverted T-shaped; the central column is composed of a cylindrical base and a cylindrical rod; a diameter of the first circular hole is equal to a diameter of the cylindrical base; and diameters of the second circular hole and the third circular hole and a diameter of the cylindrical rod are equal to one another.

Preferably, the acoustic wave transmitter is mounted between the first fixing plate and the second fixing plate; a plurality of third grooves are provided on an upper surface of the bottom steel plate; and the temperature sensors are mounted in the third grooves.

Preferably, the first grooves on the first fixing plate correspond to the second grooves on the second fixing plate, namely, the height and the number of the first grooves and the second grooves are respectively in a one-to-one correspondence; two ends of the acoustic wave transmitter are respectively fixed on the first groove of the first fixing plate and the second groove of the second fixing plate; the acoustic wave transmitters are mounted between the first fixing plate and the second fixing plate; the acoustic wave transmitters include a first acoustic wave transmitter and a second acoustic wave transmitter, respectively mounted on two sets of fixing plates arranged adjacently.

Two groups of the third grooves are arranged vertically, and are respectively configured to mount the first temperature sensor and the second temperature sensor; each group of the third grooves is arranged in a straight line, namely, the first temperature sensor and the second temperature sensor are vertically arranged on a surface of the bottom steel plate.

The acoustic wave receivers include a first acoustic wave receiver and a second acoustic wave receiver, configured to measure consolidation dynamic processes of the cement sheath in the directions of the minimum horizontal principal stress and the maximum horizontal principal stress, respectively; the first acoustic wave receiver and the second acoustic wave receiver are vertically arranged on an inner surface of the heat insulating casing, having a same height; the strain gauges include a first strain gauge and a second strain gauge; the first strain gauge and the second strain gauge are vertically arranged on the inner surface of the heat insulating casing, and are respectively configured to measure deformations of the cement sheath in the directions of the minimum horizontal principal stress and the maximum horizontal principal stress.

The first acoustic wave receiver, the first acoustic wave transmitter, and the first strain gauge in a straight line are grouped as a first group, and the second acoustic wave receiver, the second acoustic wave transmitter, and the second strain gauge in a straight line are grouped as a second group; and the first group and the second group are respectively mounted along the directions of the maximum horizontal principal stress and the minimum horizontal principal stress, namely, the pressurization directions of the two confining pressure press devices.

Preferably, the axial pressure pressurizing device and the confining pressure pressurizing device are respectively connected to an oil pump through oil pipelines; pressure gauges are provided in the oil pump; and the oil pipelines are provided with valves for controlling applied pressure.

Preferably, the axial pressure pressurizing device is located above the cavity; a fourth circular hole is provided at a center of the axial pressure pressurizing device; the diameter of the second circular hole is equal to the diameter of the cylindrical rod; a size of the axial pressure pressurizing device is matched with a size of the cavity; the axial pressure pressurizing device is sleeved on the cylindrical rod of the central column or on a heat insulating casing string.

Preferably, a fourth groove is formed by the confining pressure pressurizing device, the bottom steel plate, the heat insulating layer and the base plate, and a bottom of the detachable plate is inserted into the fourth groove.

The confining pressure pressurizing devices includes a first confining pressure pressurizing device and a second confining pressure pressurizing device, respectively located inside two adjacent sides of the housing; and the confining pressure pressurizing devices are configured to apply the maximum horizontal principal stress and the minimum horizontal principal stress.

Preferably, a filling plate is provided under a pressure transmitting plate; a sum of heights of the filling plate and the pressure transmitting plate is equal to a height of the limiting plate; during use, the filling plate is inserted in the fourth groove, and the pressure transmitting plate is located above the filling plate; the pressure transmitting plate and the filling plate constitute the detachable plate for using simultaneously, and are configured to simulate a cement sheath consolidation process; the filling plate is configured to fill the fourth groove and support the pressure transmitting plate; the pressure transmitting plate is configured to transmit the confining pressure; the limiting plates are applied to a core manufacturing process, and configured to limit horizontal displacements of the core when manufacturing the core.

The limiting plates include a first limiting plate and a second limiting plate, wherein the first limiting plate and the second limiting plate are steel plates, and respectively located at corresponding positions of two adjacent sides of the cavity.

The filling plates include a first filling plate and a second filling plate, wherein the first filling plate and the second filling plate are respectively located in the fourth grooves of the two adjacent sides of the housing; the pressure transmitting plates include a first pressure transmitting plate and a pressure second transmitting plate respectively located at the corresponding positions of the two adjacent sides of the cavity.

Preferably, the cooling device is a freezer.

Preferably, the limiting plate is provided with a pulling ring for facilitating disassembly and replacement of the steel plate.

Preferably, the heat insulating casing includes the base holder, the heat insulating casing string and an annular step, wherein the annular step is located at a bottom of the heat insulating casing string and is sleeved outside the heat insulating casing string.

A size of the base holder is equal to a size of a central column base; a height of the annular step is equal to a sum of heights of the heat insulating layer and the bottom steel plate; an outer diameter of the annular step is equal to a diameter of the cylindrical rod of the central column; an inner diameter of the annular step is equal to an outer diameter of the heat insulating casing string; the heat insulating casing string is a hollow tube filled with heat insulating materials.

The heat insulating casing is configured to simulate the function of the casing in the well cementing process in the strata; an outer diameter of the heat insulating casing string is smaller than the diameter of the cylindrical rod of the central column, namely, smaller than a diameter of a central hole of the core; a space for injecting cement to form the cement sheath is provided between the heat insulating casing string and a prepared core; the strain gauge is configured to measure strain to reflect a stress of the strata to the cement sheath; and the acoustic wave receiver is configured to receive the acoustic wave emitted by the acoustic wave transmitter to reflect the cement consolidation dynamic process.

The present invention further provides a method for preparing a frozen soil sample by using the laboratory device, including the following steps:

(1) installing a central column and a limiting plate to form a cavity for preparing a frozen soil sample;

(2) filling the cavity with wet soil uniformly mixed at a certain soil-water ratio, and compacting the wet soil by using a piston when each $\frac{1}{5}^{th}$ of the volume of the cavity is filled, until the cavity is full;

(3) fixing an axial pressure pressurizing device, and applying an axial pressure, wherein the axial pressure is equal to an overburden pressure applying to a rock at a simulated strata depth;

(4) unloading the axial pressure after stably pressurizing for half an hour, and completing a preparation of the frozen soil sample.

The present invention further provides a method for simulating a cement sheath consolidation process in the frozen soil strata by using the laboratory device. Specifically, a heat transfer of the frozen soil strata, a stress to the cement sheath by a creeping of the frozen soil and a consolidation situation of the cement sheath during a consolidation process of the cement sheath are measured by a temperature sensor, a strain gauge and an acoustic wave detecting device.

The method includes the following steps:

(1) installing a central column and a limiting plate to form a cavity for preparing a frozen soil sample;

(2) filling the cavity with wet soil uniformly mixed at a certain soil-water ratio, and compacting the wet soil by using a piston when each $\frac{1}{5}^{th}$ of the volume of the cavity is filled, until the cavity is full;

(3) fixing an axial pressure pressurizing system, and applying an axial pressure, wherein the axial pressure is equal to an overburden pressure applying to a rock at a simulated strata depth;

(4) unloading the axial pressure after stably pressurizing for half an hour, and completing a preparation of the frozen soil sample;

(5) replacing the limiting plate with a pressure transmitting plate, and replacing the central column with a heat insulating casing, wherein an annular space of the cement sheath is formed between the frozen soil sample and the heat insulating casing string;

(6) placing the laboratory device in a low temperature environment until the temperature sensor reaches a preset test temperature, and forming the frozen soil sample;

(7) setting pressures of the first confining pressure pressurizing device and the second confining pressure pressurizing device to be a strata minimum horizontal principal stress and a strata maximum horizontal principal stress, respectively, and setting the axial pressure to be the overburden pressure on the strata;

(8) injecting prepared cement into the annular space of the cement sheath;

(9) turning on the acoustic wave transmitter to measure a consolidation dynamic process of the cement sheath, measuring the stress to the cement sheath caused by the creeping of the frozen soil in the consolidation process through the strain gauge, and measuring an impact of a heat release on the temperature distribution of the frozen soil strata in the cement consolidation process;

(10) unloading the pressure, taking out the frozen soil sample, and observing a cementitious surface between the frozen soil sample and the cement sheath.

Up to now, the research on the cement sheath consolidation in the well cementing project mainly focuses on the high temperature and high pressure strata, while there is little research on the cement sheath consolidation condition in the frozen soil strata and the effect of the cement consolidation on frozen soil strata. Moreover, in the existing devices, the consolidation of the cement sheath is researched separately from the actual strata stress distribution, without consideration of the interaction between the own stress distribution of the strata and the consolidation of the cement sheath. The heat released by the cement sheath in the high temperature strata has few effects on the strata. On the contrary, the physical properties and mechanical properties of the frozen soil strata are highly affected by the temperature, thereby affecting the consolidation of the cement sheath. Therefore, the traditional device is not suitable for the research on the cement sheath consolidation process in the frozen soil strata. Compared with the previous devices applied for the analogous research, the present device has the following functions. First, the strata stress distribution is simulated by artificially fabricating the frozen soil rock sample and applying different horizontal crustal stress and overburden pressure when the cement sheath is consolidated in the actual strata. Secondly, the temperature sensor is configured to measure the effect of the heat released in the cement sheath consolidation process on the temperature distribution of the frozen soil strata. Third, the strain gauge is configured to measure the effect of the heat on the frozen soil and the stress action on the cement sheath caused by the own creep characteristic of the frozen soil. Fourth, the acoustic wave detecting device is configured to reflect the cement sheath consolidation dynamic process. The laboratory device lays an experimental foundation for further theoretical research.

The advantages of the present invention are as follows.

In the present invention, the device can artificially fabricate a frozen soil core with a hollow cylinder at the middle, and mount the heat insulating casing holder. Subsequently, the cement is added. The state of the cement sheath consolidation under the actual strata condition is simulated by applying the overburden pressure, the maximum horizontal principal stress and the minimum horizontal principal stress. Concurrently, the temperature sensor, the strain gauge and the acoustic wave measure device are configured to measure the heat transfer in the frozen soil strata in the cement sheath consolidation process, the extrusion of the cement sheath caused by the creep of the frozen soil and the consolidation of the cement sheath. The laboratory device has the advantages of having a low cost, a high efficiency, and a simple operation.

DESCRIPTIONS OF THE REFERENCE DESIGNATORS 1. central column; 2. axial pressure pressurizing device; 3. first fixing plate; 4. second fixing plate; 5. first acoustic wave transmitter; 6. housing; 7. cavity; 8. base plate; 9. first temperature sensor; 10. heat insulating layer; 11. bottom steel plate; 12. first pressure gauge; 13. first oil pump; 14. first valve; 15. first oil pipeline; 16. first confining pressure pressurizing device; 17. first limiting plate; 18. pulling ring; 19. third oil pipeline; 20. third valve; 21. third oil pump; 22. third pressure gauge; 23. second pressure gauge; 24. second oil pump; 25. second valve; 26. second oil pipeline; 27. computer; 28. base holder; 29. cement sheath annular space; 30. first filling plate; 31. first pressure transmitting plate; 32. first strain gauge; 33. second limiting plate 34. second confining pressure pressurizing device; 35. second pressure transmitting plate; 36. freezer; 37. second temperature sensor; 38. first acoustic wave receiver; 39. second acoustic wave receiver; 40. second acoustic wave transmitter; 41. second strain gauge; 42. annular step.

DETAILED DESCRIPTION OF THE EMBODIMENTS

The present invention will be further described hereinafter in conjunction with the drawings and embodiments. It should be noted that the following descriptions are merely intended to illustrate the present invention, rather than limit the content of the present invention.

Embodiment 1

A laboratory device for simulating a cement sheath consolidation in a frozen soil strata is as follows.

Figure 1:
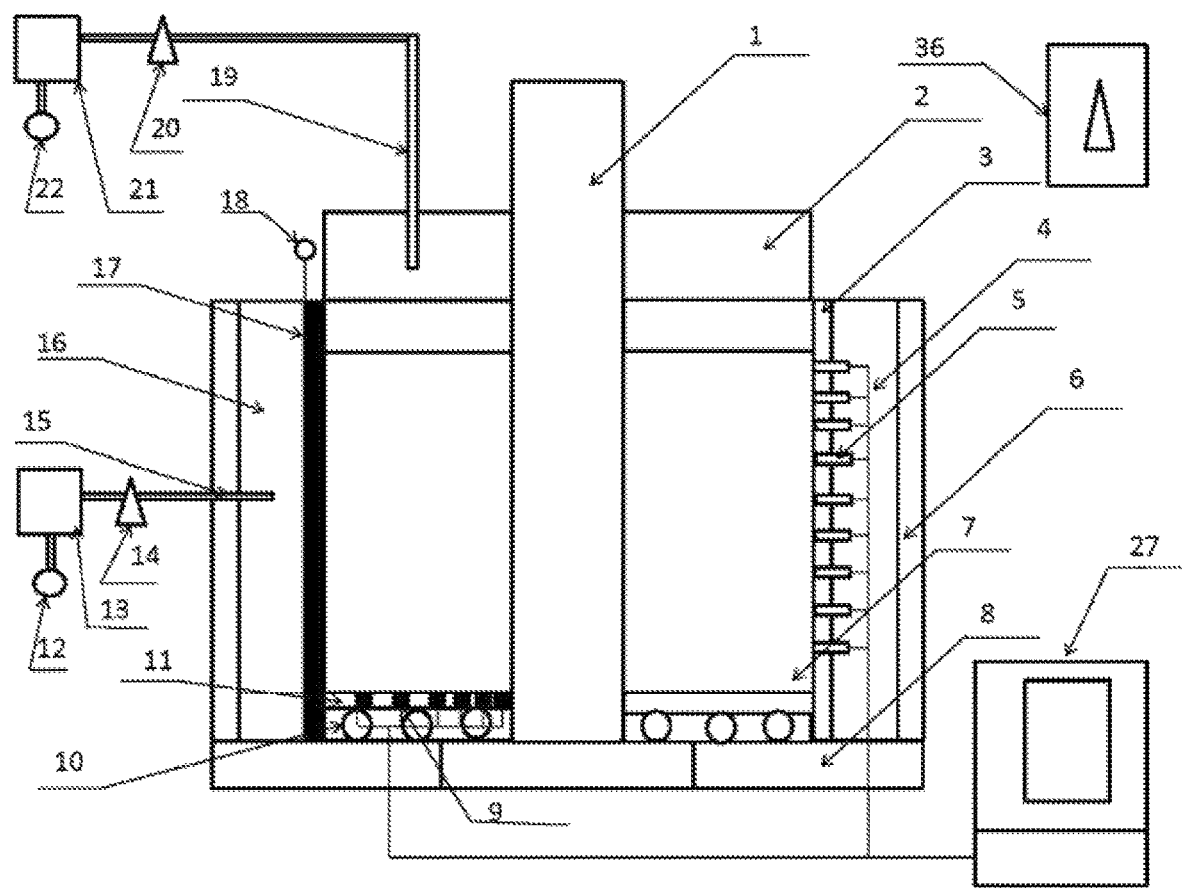
FIG. 1 is a schematic diagram of a structure of a device in a process of manufacturing a core.
Figure 2:
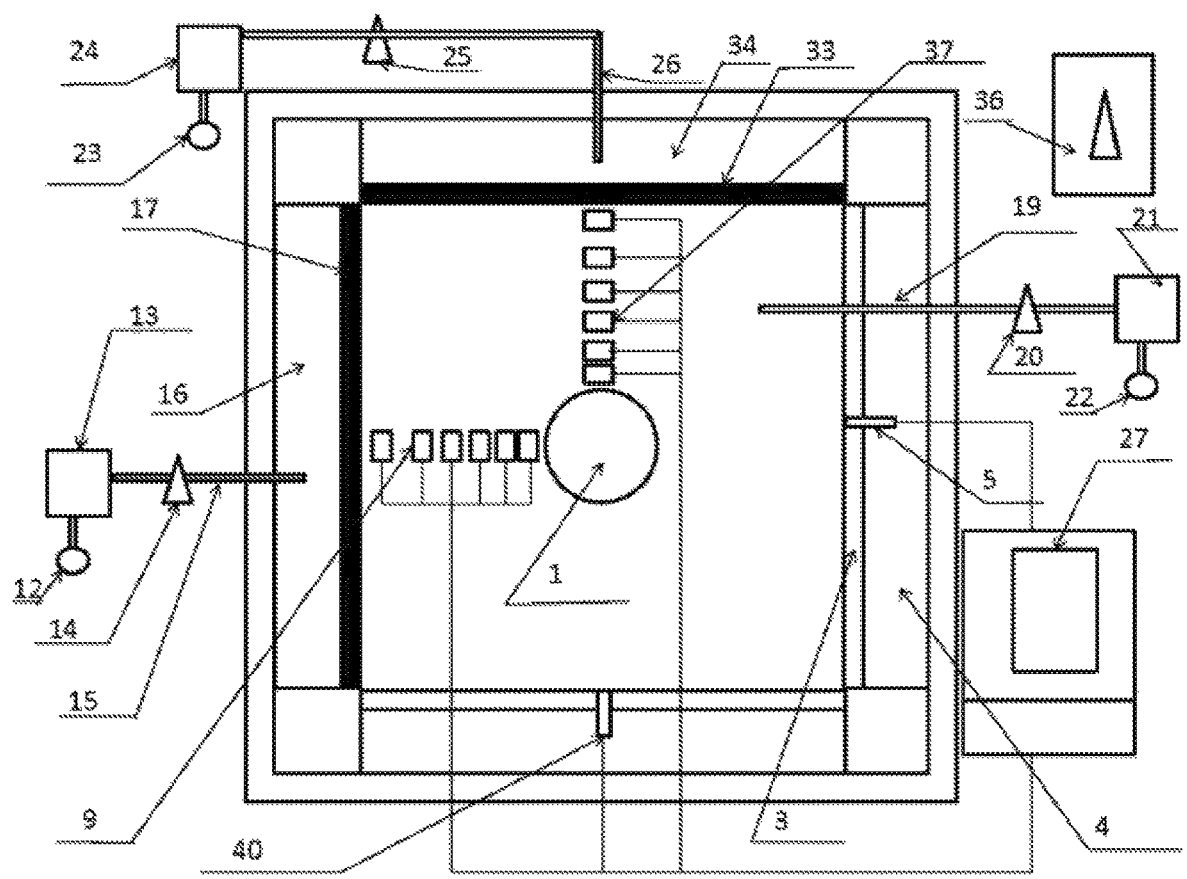
FIG. 2 is a top plan view of the structure of the device in the process of manufacturing the core.
Figure 3:
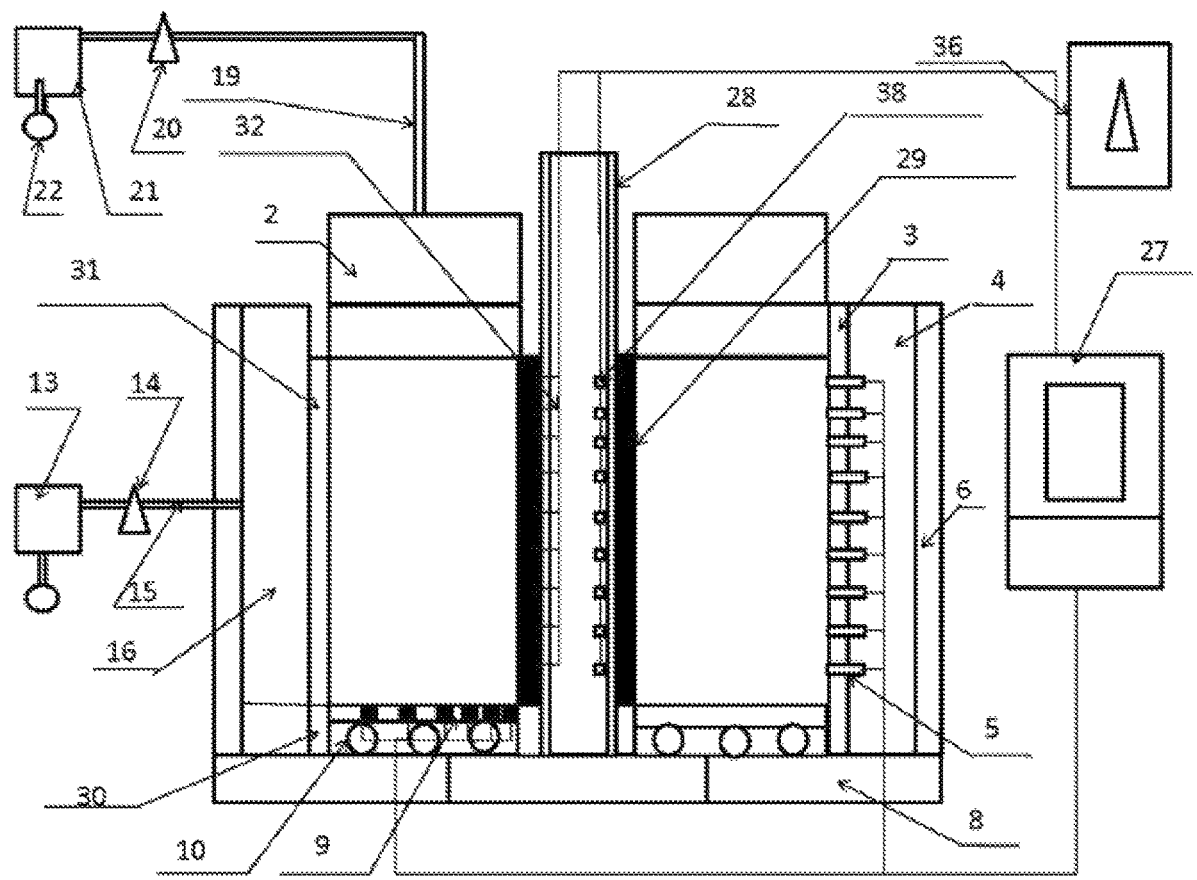
FIG. 3 is a schematic diagram of a structure of the device in a process of cement sheath consolidation.
Figure 4:
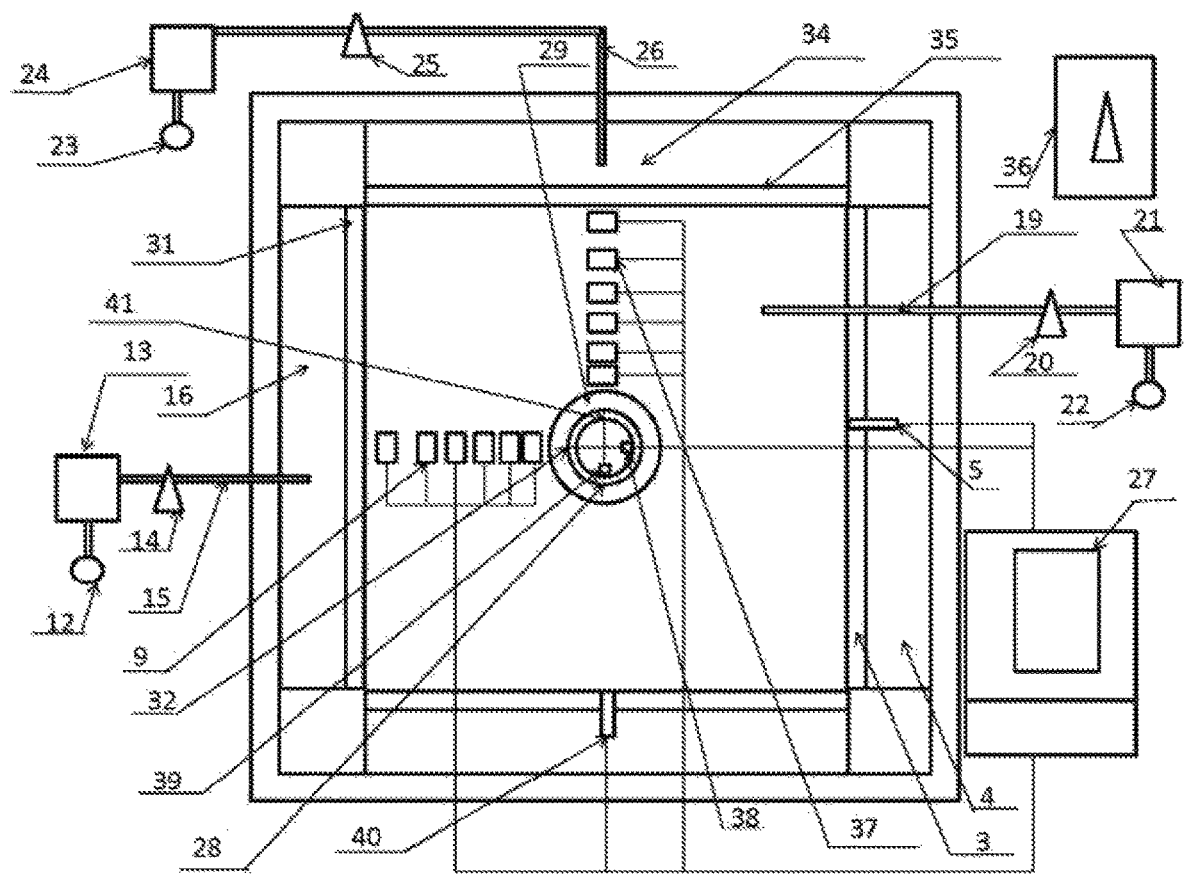
FIG. 4 is a top plan view of the structure of the device in the process of the cement sheath consolidation.
Figure 5A:
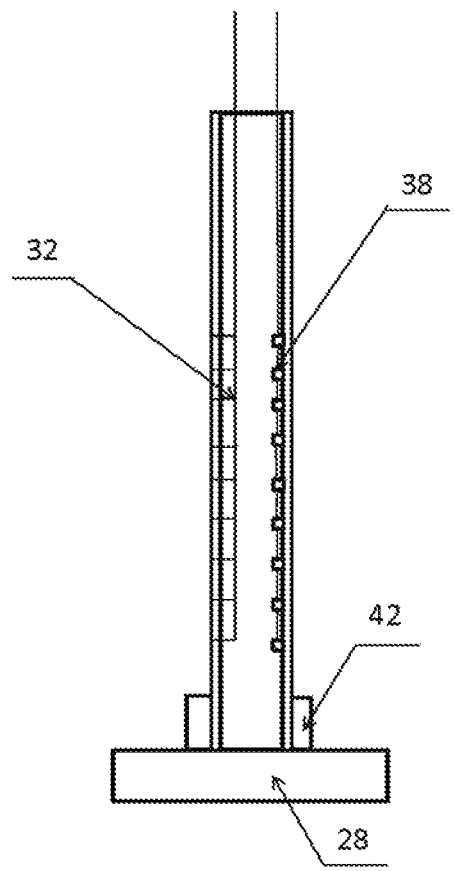
FIG. 5A is a schematic diagram of a structure of a heat insulating casing with a base holder.
Figure 5B:
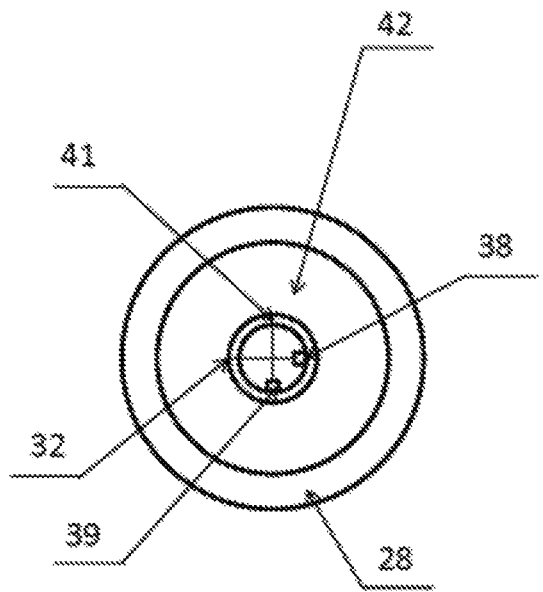
FIG. 5B is a top plan view of the structure of the heat insulating casing with the base holder.

As shown in FIG. 1 to FIG. 5B, a laboratory device for simulating a cement sheath consolidation in the frozen soil strata of Embodiment 1 of the present invention includes a main body, a pressure system and a measuring system.

The main body is square, and includes the fixing plates, the detachable plates and the base plate 8. The housing 6 is provided on the sides of the square body.

The side of the square main body is composed of two detachable plates and two sets of fixing plates. The two detachable plates are arranged adjacent to each other. The fixing plate includes the first fixing plate 3 and the second fixing plate 4. One first fixing plate 3 and one second fixing plate 4 constitutes a set of fixing plates. The first fixing plate 3 and the second fixing plate 4 are arranged in parallel. The second fixing plate 4 is located between the first fixing plate 3 and the housing 6. A plurality of first grooves and second grooves are provided on the first fixing plate 3 and the second fixing plate 4.

The bottom steel plate 11 is provided above the base plate 8. The heat insulating layer 10 is provided between the base plate 8 and the bottom steel plate 11. The cavity 7 is formed by two adjacent sets of fixing plates, two adjacent detachable plates, the bottom steel plate 11, and the central column 1 or the heat insulating casing. The cavity 7 is configured to prepare the core and the cement sheath. The detachable plate includes the limiting plate and the pressure transmitting plate.

The pressure system includes the axial pressure pressurizing device and the confining pressure pressurizing device. The axial pressure pressurizing device is located above the cavity 7. The confining pressure pressurizing device is located outside the detachable plate.

The measuring system includes the acoustic wave transmitter, the acoustic wave receiver, the temperature sensor and the strain gauge. The measuring system is connected to the computer 27. The acoustic wave transmitter is mounted on the fixing plate. The acoustic wave receiver and the strain gauge are mounted on the heat insulating casing. The temperature sensor is mounted on the base plate.

The main body, the pressure system, and the measuring system are placed in the freezer 36 during operation.

Specifically, the heat insulating casing includes the base holder 28, the heat insulating casing string and the annular step 42. The annular step 42 is located at the bottom of the heat insulating casing string, and is sleeved outside the heat insulating casing string.

Specifically, the center column 1 or the heat insulating casing is located at the center of the cavity 7. The longitudinal section of the center column 1 is inverted T-shaped. The center column 1 is composed of the cylindrical base and the cylindrical rod. The diameter of the first circular hole is equal to the diameter of the cylindrical base. The diameters of the second circular hole and the third circular hole and the diameter of the cylindrical rod are equal to one another.

Specifically, the acoustic wave transmitter is mounted between the first fixing plate 3 and the second fixing plate 4. The acoustic wave receiver and the strain gauge are provided inside the heat insulating casing string. The plurality of third grooves is provided on the upper surface of the bottom steel plate 11. The temperature sensor is mounted in the third groove.

Specifically, the first groove on the first fixing plate 3 corresponds to the second groove on the second fixing plate 4, namely, the height and the number of the first fixing plate 3 and the second fixing plate 4 are in one-to-one correspondence. Two ends of the acoustic wave transmitter are respectively fixed on the first groove of the first fixing plate 3 and the second groove of the second fixing plate 4. The acoustic wave transmitter includes the first acoustic wave transmitter 5 and the second acoustic wave transmitter 40. The first acoustic wave transmitter 5 and the second acoustic wave transmitter 40 are respectively mounted at the corresponding positions of the two adjacent sides of the cavity, namely, in the grooves of the fixing plate.

The third grooves are grouped as two groups arranged vertically, and configured to mount the first temperature sensor 9 and the second temperature sensor 37, respectively. Each group of third grooves is arranged in a line, namely, the first temperature sensor 9 and the second temperature sensor 37 are vertically arranged on the surface of the bottom steel plate 11.

The acoustic wave receiver includes the first acoustic wave receiver 38 and the second acoustic wave receiver 39 for measuring the dynamic change processes of the cement sheath in the minimum horizontal principal stress direction and the maximum horizontal principal stress direction, respectively. The first acoustic wave receiver 38 and the second acoustic wave receiver 39 are vertically arranged on the inner surface of the heat insulating casing string at the same height; the strain gauge includes the first strain gauge 32 and the second strain gauge 41. The first strain gauge 32 and the second strain gauge 41 are vertically provided on the inner surface of the heat insulating casing string.

The first acoustic wave receiver 38, the first acoustic wave transmitter 5, and the first strain gauge 32 are in a line, and the second acoustic wave receiver 39, the second acoustic wave transmitter 40, and the second strain gauge 41 are in a line, namely, the first acoustic wave receiver 38 and the second acoustic wave receiver 39 are vertically arranged; the first strain gauge 32 and the second strain gauge 41 are vertically arranged; the first acoustic wave transmitter 5 and the first acoustic wave receiver 4 are correspondingly mounted; and the second acoustic wave transmitter 40 and the second acoustic wave receiver 39 are correspondingly mounted.

The first strain gauge 32 and the second strain gauge 41 are configured to measure the deformations of the cement sheath in the directions of the minimum horizontal principal stress and the maximum horizontal principal stress, respectively.

Specifically, the axial pressure pressurizing device and the confining pressure pressurizing device are respectively connected to the oil pumps through oil pipelines. The oil pumps are provided with the pressure gauges. The oil pipelines are provided with valves for controlling the pressurization pressure.

Specifically, the axial pressure pressurizing device is located above the cavity 7. The fourth circular hole is provided at the center of the axial pressure pressurizing device. The diameter of the second circular hole is equal to the diameter of the cylindrical rod. The size of the device is matched with the size of the cavity. During use, the axial pressure pressurizing device is placed on the cylindrical rod of the central column 1, or on the heat insulating casing string.

Specifically, the fourth groove is formed by the confining pressure pressurizing device, the bottom steel plate 11, the heat insulating layer 10, and the base plate 8. The bottom of the detachable plate is inserted into the fourth groove.

The confining pressure pressurizing device includes the first confining pressure pressurizing device 16 and the second confining pressure pressurizing device 34, respectively located on the inner sides of the two adjacent sides of the housing. The confining pressure pressurizing device is configured to apply the maximum horizontal principal stress and the minimum horizontal principal stress.

Specifically, the first confining pressure pressurizing device 16 is connected to the first oil pump 13 through the first oil pipeline 15. The first oil pump 13 is provided with the first pressure gauge 12. The first oil pipeline 15 is provided with the first valve 14.

The second confining pressure pressurizing device 34 is connected to the second oil pump 24 through the second oil pipeline 26. The second oil pump 24 is provided with the second pressure gauge 23. The second oil pipeline 26 is provided with the second valve 25.

The axial pressure pressurizing device 2 is connected to the third oil pump 21 through the third oil pipeline 19. The third oil pump 21 is provided with the third pressure gauge 22. The third oil pipeline 19 is provided with the third valve 20.

Specifically, the filling plate is provided closely below the pressure transmitting plate. The sum of the heights of the filling plate and the pressure transmitting plate is equal to the height of the limiting plate. During use, the filling plate is inserted in the fourth groove, and the pressure transmitting plate is located on the filling plate. The pressure transmitting plate and the filling plate form the detachable plate for simultaneous use, and are used to simulate the cement sheath consolidation process. The filling plate functions to fill the fourth groove, and to support the pressure transmitting plate. The pressure transmitting plate functions to transmit the confining pressure. The limiting plate is configured for the core manufacturing process, and functions to prevent the horizontal displacement of the core during the core manufacturing process.

In the present invention, the limiting plate cannot replace the pressure transmitting steel plate. The pressure transmitting steel plate will apply stress to the frozen soil by moving after being compressed. The limiting plate cannot apply stress since the lower end thereof is fixed. In the consolidation process, the frozen soil sample is constricted from all sides and the upper portion thereof is subjected to the load. As a result, the limiting plate is employed. If the confining pressure pressurizing device is configured to limit the horizontal displacement of the core, the service life of the confining pressure pressurizing device will be reduced.

The limiting plate includes the first limiting plate 17 and the second limiting plate 33, which are steel plates, and respectively located on two adjacent sides of the cavity.

The filling plate includes the first filling plate 30 and the second filling plate, which are respectively located in the fourth grooves of two adjacent sides of the cavity. The pressure transmitting plate includes the first pressure transmitting plate 31 and the second pressure transmitting plate 35, which are respectively located on two adjacent sides of the cavity.

Specifically, the limiting plate is provided with the pulling ring 18, which facilitates to disassemble and replace the steel plate.

Embodiment 2

The method for preparing the frozen soil sample is as follows.

a. A layer of grease is coated on the surface of the central column 1. The central column 1 is inserted from the first circular hole of the base plate 8 from below. The device is posed upright.

b. The first limit plate 17, the second limit plate 33 are respectively inserted into the fourth grooves of the adjacent two sides of the cavity. The cavity 7 is formed by the first limit plate 17, the second limit plate 33, the bottom steel plate 11, and the two adjacent first fixing plates 3.

c. The wet soil uniformly mixed at a certain soil-water ratio is slowly filled into the cavity 7. When each $1/5^{th}$ of the volume of the cavity is filled, the wet soil is compacted by using the square piston with the circular hole in the middle until the cavity is full.

d. The axial pressure pressurizing device 2 is placed at the fixing position above the cavity 7, and is supported by the compacted wet soil.

e. The third valve 20 and the third oil pump 21 are opened. The pressure is applied to the axial pressure pressurizing device 2 through the third oil pipeline 19. The pressure is equal to the overburden pressure applied to the rock at the simulated strata depth.

f. After stably applying the pressure for half an hour, the axial pressure is unloaded. The axial pressure pressurizing device 2 is taken out. The preparation of the frozen soil sample is completed.

Embodiment 3

The method for simulating the cement sheath consolidation process in the frozen soil strata is as follows:

1) After the preparation of the frozen soil sample is completed, the first limiting plate 17, the second limiting plate 33 are pulled out by the pulling ring 18, and the filling plate is mounted into the fourth groove. Then, the first pressure transmitting plate 31 and the second pressure transmitting plate 35 are placed into the device.

2) The prepared central column 1 of the core is taken out, and the heat insulating casing with the base holder is mounted from the bottom of the base plate 8. The cement sheath annular space 29 is formed between the frozen soil sample and the heat insulating casing string. Under the creeping action of the frozen soil, a little cement may spill, which proves that the creep of the frozen soil has the extrusion effect on the consolidation of the cement sheath.

3) The temperature of the freezer is set as the test temperature, and then the computer 27 is turned on until all the temperature sensors display the set temperature of the freezer, thereby forming the frozen soil sample. The whole device is placed in the freezer, and the temperature of the freezer 36 is adjusted. Then, the device is kept aside, and the readings in the various temperature sensors can be observed. When the readings are equal to the temperature of the freezer, it can be regarded that the frozen soil state at this temperature has been achieved.

4) The axial pressure pressurizing device 2 is placed at the fixing position above the cavity 7 again, and is supported by the frozen soil sample.

5) The first valve 14 and the first oil pump 13 are opened to set the pressure of the first confining pressure pressurizing device 16 as the minimum horizontal principal stress of the strata, and the first confining pressure pressurizing device 16 is pressurized through the first oil pipeline 15.

6) The second valve 25 and the second oil pump 24 are opened. Then, the pressure of the second confining pressure pressurizing device 34 is set as the maximum horizontal principal stress of the strata, and the second confining pressure pressurizing device 34 is pressurized by the second oil pipeline 26.

7) The third valve 20 and the third oil pump 21 are opened. The axial pressure is set as the overburden pressure of the strata, and the axial pressure pressurizing device 2 is pressurized by the third oil pipeline 19.

8) The prepared cement is injected into the cement sheath annular space 29.

9) The first acoustic wave transmitter 5 and the second acoustic wave transmitter 40 are turned on to measure the consolidation dynamic process of the cement sheath. The extrusion of the cement sheath caused by the creep of the frozen soil in the consolidation process is measured by the first strain gauge 32 and the second strain gauge 41. The effect on the temperature distribution of the frozen soil strata due to the heat released during the cement consolidation process is measured by the first temperature sensor 9 and the second temperature sensor 37.

10) The axial pressure is unloaded, the third oil pump 21 and the third valve 20 are closed, and the axial pressure pressurizing device 2 is taken out. Then, the first confining pressure (maximum horizontal principal stress) is unloaded, the first oil pump 13 and the first valve 14 are closed, and the first pressure transmitting steel plate 31 is taken out. The second confining pressure (minimum horizontal principal stress) is unloaded, the second oil pump 24 and the second valve 25 are closed, and the second pressure transmitting steel plate 35 is taken out.

11) The sample is taken out to obverse the cementitious surface between the frozen soil and the cement sheath.

Despite the specific embodiments of the present invention have been described above with reference to the drawings, it is not intended to limit the protection scope of the present invention. Based on the technical solution of the present invention, various modifications or variations made by the person skilled in the art without creative efforts are still within the protection scope of the present invention.

What is claimed is:

1. A laboratory device for simulating a cement sheath consolidation in frozen soil strata, comprising: a main body, a pressure system and a measuring system; wherein
   the main body comprises fixing plates, detachable plates and a base plate; a circular hole is provided in a center of a base holder; a central column or a heat insulating casing is mounted on the base through the circular hole; a cavity for preparing a core and a cement sheath is formed by the fixing plates, the detachable plates, the base plate and the central column or the heat insulating casing; the detachable plate comprises limiting plates and pressure transmitting plates;
   the pressure system comprises an axial pressure pressurizing device and confining pressure pressurizing devices, the axial pressure pressurizing device is located above the cavity, and the confining pressure pressurizing devices are located outside the detachable plates; and
   the measuring system comprises acoustic wave transmitters, acoustic wave receivers, temperature sensors and strain gauges, the measuring system is connected to a controller; the acoustic wave transmitters are mounted on the fixing plates; the acoustic wave receivers and the strain gauges are mounted on the heat insulating casing; the temperature sensors are mounted on the base plate.

2. The laboratory device for simulating the cement sheath consolidation in the frozen soil strata according to claim 1, wherein the main body is a square; sides of the main body are composed of two detachable plates and two adjacent sets of fixing plates; the two detachable plates are adjacently arranged; a bottom steel plate is provided above the base plate; a heat insulating layer is provided between the base plate and the bottom steel plate; a cavity is formed by the two adjacent sets of fixing plates, two adjacent detachable plates, the bottom steel plate, and the central column or the heat insulating casing.

3. The laboratory device for simulating the cement sheath consolidation in the frozen soil strata according to claim 1, wherein the fixing plates comprise a first fixing plate and a second fixing plate, wherein the first fixing plate and the second fixing plate form a set of fixing plates; the first fixing plate and the second fixing plate are arranged in parallel to each other; the second fixing plate is located between the first fixing plate and a housing; a plurality of first grooves and second grooves are provided on the first fixing plate and the second fixing plate; the housing is provided on the sides of the main body, and the confining pressure pressurizing devices are located between the detachable plates and the housing.

4. The laboratory device for simulating the cement sheath consolidation in the frozen soil strata according to claim 2, wherein a first circular hole, a second circular hole and a third circular hole are respectively provided in centers of the base plate, the bottom steel plate and the heat insulating layer; the central column or the heat insulating casing is located at a center of the cavity; a longitudinal section of the central column is inverted T-shaped; the central column is composed of a cylindrical base and a cylindrical rod; a diameter of the first circular hole is equal to a diameter of the cylindrical base; and diameters of the second circular hole and the third circular hole and a diameter of the cylindrical rod are equal to one another.

5. The laboratory device for simulating the cement sheath consolidation in the frozen soil strata according to claim 3, wherein the first grooves on the first fixing plate correspond to the second grooves on the second fixing plate, wherein heights and numbers of the first grooves and the second grooves are in one-to-one correspondence; two ends of the acoustic wave transmitter are respectively fixed on the first grooves on the first fixing plate and the second grooves on the second fixing plate; the acoustic wave transmitters comprise a first acoustic wave transmitter and a second acoustic wave transmitter, respectively mounted on the two adjacent sets of fixing plates; the acoustic wave receivers comprise a first acoustic wave receiver and a second acoustic wave receiver; and the first acoustic wave receiver and the second acoustic wave receiver are vertically arranged on an inner surface of the heat insulating casing at a same height.

6. The laboratory device for simulating the cement sheath consolidation in the frozen soil strata according to claim 2, wherein the temperature sensor comprises a first temperature sensor and a second temperature sensor; a plurality of third grooves are provided on an upper surface of the bottom steel plate; the plurality of third grooves are grouped as two groups vertically arranged, and configured to respectively mount the first temperature sensor and the second temperature sensor.

7. The laboratory device for simulating the cement sheath consolidation in the frozen soil strata according to claim 1, wherein the axial pressure pressurizing device and the confining pressure pressurizing devices are respectively connected to oil pumps through oil pipelines; pressure gauges are provided on the oil pumps; and the oil pipelines are provided with valves.

8. The laboratory device for simulating the cement sheath consolidation in the frozen soil strata according to claim 3, wherein a fourth groove is formed by the confining pressure pressurizing devices, the bottom steel plate, the heat insulating layer and the base plate, and the detachable plates are fixed by the fourth groove.

9. The laboratory device for simulating the cement sheath consolidation in the frozen soil strata according to claim 1, wherein the heat insulating casing comprises the base holder, a heat insulating casing string and an annular step; the annular step is located at a bottom of the heat insulating casing string and is sleeved outside the heat insulating casing string; a size of the base holder is equal to a size of a central column base; a height of the annular step is equal to a sum of heights of the heat insulating layer and the bottom steel plate; an outer diameter of the annular step is equal to a diameter of the cylindrical rod of the central column; an inner diameter of the annular step is equal to an outer diameter of the heat insulating casing string; the heat insulating casing string is a hollow tube filled with heat insulating materials.

10. A method for simulating a cement sheath consolidation process in frozen soil strata by using the laboratory device according to claim 1, comprising the following steps:
    (1) installing the central column and the limiting plate to form the cavity for preparing a frozen soil sample;
    (2) filling the cavity with wet soil uniformly mixed at a certain soil-water ratio, and compacting the wet soil by using a piston when each $\frac{1}{5}^{th}$ of the volume of the cavity is filled, until the cavity is full;
    (3) fixing the axial pressure pressurizing system, and applying an axial pressure, wherein the axial pressure is equal to an overburden pressure applied to a rock at a simulated strata depth;
    (4) unloading the axial pressure after stably pressurizing for half an hour, and completing a preparation of the frozen soil sample;
    (5) replacing the limiting plate with the pressure transmitting plate, and replacing the central column with the heat insulating casing, wherein an annular space of the cement sheath is formed between the frozen soil sample and the heat insulating casing string;
    (6) placing the laboratory device in a low temperature environment until the temperature sensor reaches a preset test temperature, and forming the frozen soil sample;
    (7) setting pressures of the first confining pressure pressurizing device and the second confining pressure pressurizing device to be a strata minimum horizontal principal stress and a strata maximum horizontal principal stress, respectively, and setting the axial pressure to be the overburden pressure of the strata;
    (8) injecting prepared cements into the annular space of the cement sheath;
    (9) turning on the acoustic wave transmitter to measure a consolidation dynamic process of the cement sheath, measuring the extrusion of the cement sheath caused by the creeping of the frozen soil in the consolidation process through the strain gauge, and measuring an impact on the temperature distribution of the frozen soil strata caused by a heat release in the cement consolidation process through the temperature sensor;
    (10) unloading the pressure, taking out the frozen soil sample, and observing a cementitious surface between the frozen soil sample and the cement sheath.

11. The laboratory device for simulating the cement sheath consolidation in the frozen soil strata according to claim 2, wherein the fixing plates comprise a first fixing plate and a second fixing plate, wherein the first fixing plate and the second fixing plate form a set of fixing plates; the first fixing plate and the second fixing plate are arranged in parallel; the second fixing plate is located between the first fixing plate and a housing; a plurality of first grooves and second grooves are provided on the first fixing plate and the second fixing plate; the housing is provided on the sides of the main body, and the confining pressure pressurizing devices are located between the detachable plates and the housing.

12. The laboratory device for simulating the cement sheath consolidation in the frozen soil strata according to claim 11, wherein the first grooves on the first fixing plate correspond to the second grooves on the second fixing plate, wherein heights and numbers of the first grooves and the second grooves are in one-to-one correspondence; two ends of the acoustic wave transmitter are respectively fixed on the first grooves on the first fixing plate and the second grooves on the second fixing plate; the acoustic wave transmitters comprise a first acoustic wave transmitter and a second acoustic wave transmitter, respectively mounted on the two adjacent sets of fixing plates; the acoustic wave receivers comprise a first acoustic wave receiver and a second acoustic wave receiver; and the first acoustic wave receiver and the second acoustic wave receiver are vertically arranged on an inner surface of the heat insulating casing at a same height.

13. The laboratory device for simulating the cement sheath consolidation in the frozen soil strata according to claim 11, wherein a fourth groove is formed by the confining pressure pressurizing devices, the bottom steel plate, the heat insulating layer and the base plate, and the detachable plates are fixed by the fourth groove.

14. The method for simulating the cement sheath consolidation process in the frozen soil strata according to claim 10, wherein the main body is a square; sides of the main body are composed of two detachable plates and two adjacent sets of fixing plates; the two detachable plates are adjacently arranged; a bottom steel plate is provided above the base plate; a heat insulating layer is provided between the base plate and the bottom steel plate; a cavity is formed by the two adjacent sets of fixing plates, two adjacent detachable plates, the bottom steel plate, and the central column or the heat insulating casing.

15. The method for simulating the cement sheath consolidation process in the frozen soil strata according to claim 10, wherein the fixing plates comprise a first fixing plate and a second fixing plate, wherein the first fixing plate and the second fixing plate form a set of fixing plates; the first fixing plate and the second fixing plate are arranged in parallel; the second fixing plate is located between the first fixing plate and a housing; a plurality of first grooves and second grooves are provided on the first fixing plate and the second fixing plate; the housing is provided on the sides of the main body, and the confining pressure pressurizing devices are located between the detachable plates and the housing.

16. The method for simulating the cement sheath consolidation process in the frozen soil strata according to claim 14, wherein a first circular hole, a second circular hole and a third circular hole are respectively provided in centers of the base plate, the bottom steel plate and the heat insulating layer; the central column or the heat insulating casing is located at a center of the cavity; a longitudinal section of the central column is inverted T-shaped; the central column is composed of a cylindrical base and a cylindrical rod; a diameter of the first circular hole is equal to a diameter of the cylindrical base; and diameters of the second circular hole and the third circular hole and a diameter of the cylindrical rod are equal to one another.

17. The method for simulating the cement sheath consolidation process in the frozen soil strata according to claim 15, wherein the first grooves on the first fixing plate correspond to the second grooves on the second fixing plate, wherein heights and numbers of the first grooves and the second grooves are in one-to-one correspondence; two ends of the acoustic wave transmitter are respectively fixed on the first grooves on the first fixing plate and the second grooves on the second fixing plate; the acoustic wave transmitters comprise a first acoustic wave transmitter and a second acoustic wave transmitter, respectively mounted on the two adjacent sets of fixing plates; the acoustic wave receivers comprise a first acoustic wave receiver and a second acoustic wave receiver; and the first acoustic wave receiver and the second acoustic wave receiver are vertically arranged on an inner surface of the heat insulating casing at a same height.

18. The method for simulating the cement sheath consolidation process in the frozen soil strata according to claim 14, wherein the temperature sensor comprises a first temperature sensor and a second temperature sensor; a plurality of third grooves are provided on an upper surface of the bottom steel plate; the plurality of third grooves are grouped as two groups vertically arranged, and configured to respectively mount the first temperature sensor and the second temperature sensor.

19. The method for simulating the cement sheath consolidation process in the frozen soil strata according to claim 10, wherein the axial pressure pressurizing device and the confining pressure pressurizing devices are respectively connected to oil pumps through oil pipelines; pressure gauges are provided on the oil pumps; and the oil pipelines are provided with valves.

20. The method for simulating the cement sheath consolidation process in the frozen soil strata according to claim 15, wherein a fourth groove is formed by the confining pressure pressurizing devices, the bottom steel plate, the heat insulating layer and the base plate, and the detachable plates are fixed by the fourth groove.

* * * * *